(12) United States Patent
Hlavinka et al.

(10) Patent No.: US 7,964,048 B2
(45) Date of Patent: Jun. 21, 2011

(54) HEAT WELD TUBING CONNECTORS

(75) Inventors: Dennis J. Hlavinka, Arvada, CO (US);
Keith Manica, Lakewood, CO (US);
Frank Corbin, III, Littleton, CO (US);
Terrence M. Cussen, Englewood, CO (US)

(73) Assignee: CaridianBCT, Inc., Lakewood, CO (US)

( * ) Notice: Subject to any disclaimer, the term of this patent is extended or adjusted under 35 U.S.C. 154(b) by 973 days.

(21) Appl. No.: 11/772,337

(22) Filed: Jul. 2, 2007

(65) Prior Publication Data

US 2008/0009833 A1 Jan. 10, 2008

Related U.S. Application Data

(60) Provisional application No. 60/819,446, filed on Jul. 7, 2006.

(51) Int. Cl.
*B29C 65/18* (2006.01)
(52) U.S. Cl. ...... 156/158; 156/289; 156/304.6; 156/309.6; 156/503
(58) Field of Classification Search ...... 156/158, 156/289, 304.2, 304.6, 309.6, 503
See application file for complete search history.

(56) References Cited

U.S. PATENT DOCUMENTS

| | | | |
|---|---|---|---|
| 3,801,409 A * | 4/1974 | Plate et al. ...... 156/515 |
| 4,369,779 A | 1/1983 | Spencer |
| 4,412,835 A | 11/1983 | Spencer |
| 4,443,215 A | 4/1984 | Smith |
| 4,507,119 A | 3/1985 | Spencer |
| 4,516,971 A | 5/1985 | Spencer |
| 4,610,670 A | 9/1986 | Spencer |
| 4,737,214 A * | 4/1988 | Leurink et al. ...... 156/158 |
| 4,828,557 A | 5/1989 | Persidsky |
| 4,983,161 A | 1/1991 | Dadson et al. |
| 5,098,371 A | 3/1992 | Juji et al. |
| 5,158,630 A * | 10/1992 | Shaposka et al. ...... 156/158 |
| 5,167,656 A | 12/1992 | Lynn |
| 5,209,800 A * | 5/1993 | Spencer et al. ...... 156/158 |
| 5,269,350 A | 12/1993 | Galloway |
| 5,300,060 A | 4/1994 | Nelson |
| 5,345,070 A | 9/1994 | Hlavinka et al. |
| 5,672,364 A * | 9/1997 | Kato et al. ...... 425/89 |
| 5,702,383 A | 12/1997 | Geisler et al. |
| 5,921,965 A | 7/1999 | Blei |
| 6,026,882 A | 2/2000 | Yamada et al. |
| 6,341,637 B1 | 1/2002 | Yamada et al. |
| 6,626,884 B1 | 9/2003 | Dillon et al. |
| 6,679,529 B2 | 1/2004 | Johnson et al. |
| 2003/0089446 A1 * | 5/2003 | Baradon et al. ...... 156/158 |

(Continued)

FOREIGN PATENT DOCUMENTS

DE 2211548 12/1972

(Continued)

OTHER PUBLICATIONS

PCT/US2007/072562, "PCT Invitation to Pay Additional Fees" (including International Search Report), Dec. 14, 2007.

(Continued)

*Primary Examiner* — Michael A Tolin
(74) *Attorney, Agent, or Firm* — John R. Merkling; Edna M. O'Connor; Laura B. Arciniege (57) ABSTRACT

The present invention provides thermoplastic tubes, thermoplastic melting plates, thermoplastic tube connecting apparatus, and methods for using the same.

11 Claims, 6 Drawing Sheets

U.S. PATENT DOCUMENTS

2005/0211373 A1    9/2005    Tomasetti et al.

FOREIGN PATENT DOCUMENTS

| DE | 4416518 | 11/1995 |
| --- | --- | --- |
| EP | 0312712 | 4/1989 |
| EP | 0723 851 | 7/1996 |
| JP | 05272690 | 10/1993 |
| NL | 6412575 | 5/1966 |
| WO | WO82/02528 | 8/1982 |
| WO | WO02/087491 | 11/2002 |

OTHER PUBLICATIONS

PCT/US2007/072562, "International Search Report with Written Opinion", Jan. 2, 2008.

* cited by examiner

HEAT WELD TUBING CONNECTORS

CROSS-REFERENCE TO RELATED APPLICATIONS

This application claims the priority benefit of U.S. Provisional Application No. 60/819,446, filed Jul. 7, 2006, which is incorporated herein by reference in its entirety.

FIELD OF THE INVENTION

The invention relates to thermoplastic tubes, thermoplastic melting plates, thermoplastic tube connecting apparatus, and methods for using the same.

BACKGROUND OF THE INVENTION

Containers with tubing are used for various medical procedures such as kidney dialysis, intravenous delivery of therapeutic fluids, delivery of nutritional fluids; delivery of blood, blood components, and blood substitutes. Particularly in blood banking connections are frequently used between the containers and associated tubing. Such applications may require connecting two or more different containers to one another each of which typically contains a different sterile material. For example, in the blood-banking environment, a bag containing sterile solution may be connected to an apheresis kit containing tubing. Regardless of any particular application, in most cases connections between two tubes are formed.

Connecting the tubing typically involves using a sterile tube welding machine to weld the thermoplastic tubing in a sterile manner. There are many sterile tube welding machines known to one skilled in the art. One type of tube welding machine sterilizes a cutting blade or wafer then moves the blade through the two ends of the tubing to be joined. Once both ends of the tubing have been cut, the machine aligns the ends of the tubes while maintaining a high temperature. After the thermoplastic tubes cool, a sterile weld is formed. Other tube connection systems have applied heat to the ends of the tubing sections without requiring direct contact of heating elements with the tubing sections. See, for example, U.S. patent application Ser. No. 10/061,835, filed Jan. 31, 2002; Ser. No. 10/251,681, filed Sep. 20, 2002; Ser. No. 10/251,682, filed Sep. 20, 2002; and Ser. No. 10/251,683, filed Sep. 20, 2002, all of which are incorporated herein by reference in their entirety. Regardless of the type of tube welding device utilized, connecting the ends of the tube sections requires a precise alignment of the tube ends due to the relatively small wall thickness of the tube.

Sterile tube welding devices may have a relatively low level of reliability due to the inconsistency in aligning the tube ends following the melting and cutting processes. The inconsistency of operation can result in imperfect seals, leading to leaks, and microorganism infiltration which may lead to infection. In addition, the interior passages of the tubing sections are initially sterile, but in some instances cutting the tubing sections so that connections of adjacent sections can be made exposes the interior passages of the tubing sections to the surrounding environment, allowing them to potentially become contaminated with airborne contaminants, e.g., bacteria. In order to avoid exposure of the interior passage (i.e., lumen) of each tubing section, some tube welding devices clamp the end portion of the tubing section shut before an end portion of the tubing section is cut.

In some systems a hot blade or other heated surface is brought into contact with the tubing sections to bring them up to melting temperature. The ends of the two tubing sections are then brought together so that the melted ends fuse, connecting the tubing sections together. The clamps collapsing the respective end portions of the tubing sections are released and the tubing sections open, defining a continuous, sealed interior passage through the connected tubing sections. Unfortunately, the connection must often be manually opened and/or examined to ensure proper seal, thereby increasing the time and labor.

For tube welding devices that utilize a hot plate for producing molten thermoplastic and welding molten tubes, another disadvantage is that in time the hot plate becomes fouled with the plastic material, e.g., some thermoplastic resin may adhere to the hot plate, requiring occasional cleaning of the hot plate to maintain sterile operating conditions or using disposable cutting blades, thereby increasing the overall time and cost.

Accordingly, there is a need for various improvements in thermoplastic tube weld connecting devices.

SUMMARY OF THE INVENTION

One aspect of the present invention provides a thermoplastic tube comprising an inner diameter, an outer diameter, and a sealed end. The cross section defined by the outer diameter of the thermoplastic tube of the present invention is substantially greater proximal to the sealed end relative to the cross section distal to the sealed end. In addition, the wall thickness defined by difference between the outer and the inner diameter is substantially greater proximal to the sealed end relative to the wall thickness distal to the sealed end.

In some embodiments, the wall thickness proximal to the sealed end is at least about 50% greater than the wall thickness distal to the sealed end. Within these embodiments, the wall thickness proximal to the sealed end is at least 250%, and in another embodiments it is at least 350%, greater than the wall thickness distal to the sealed end.

In other embodiments, the wall thickness of the thermoplastic tube proximal to the sealed end is at least about 0.8 mm. Within these embodiments, typical wall thickness proximal to the sealed end is from about 1.1 mm to about 1.4 mm. In further embodiments the wall thickness proximal to the sealed end is at least about 2 mm.

In some embodiments, the sealed end comprises a thermoplastic cap having inserted therein a thermoplastic tube. In these embodiments, the thermoplastic cap and the thermoplastic tube are hermetically sealed to form the sealed end. Within these embodiments, in some instances, the thermoplastic cap comprises a flange. The melting temperature of the thermoplastic cap and the thermoplastic tube can be the same or different. In some instances, the melting temperature of the thermoplastic cap is different than the thermoplastic tube. In one embodiment, the melting temperature of the thermoplastic cap is lower than the melting temperature of the thermoplastic tube. Typically, the melting temperature of the thermoplastic cap is about 20 to 100° C. lower than the melting temperature of the thermoplastic tube.

In some embodiments the thermoplastic tube inserted in the thermoplastic cap is co-extruded from two thermoplastic materials having different melt temperatures. Typically, the melting temperature of the tubing inner layer is about 20 to 100° C. higher than the melting temperature of the outer layer and the cap. Exemplary instances include a tubing comprising polyolefin inner layer with PVC outer layer (available from Kelcourt Plastics Inc.), and a tubing dual layer PVC comprising a high durometer inner layer PVC and a lower durometer outer layer. In some of these particular embodiments, the thickness of inner layer can be varied to yield desired self opening performance.

As mentioned above, in one embodiment the thermoplastic tube further comprises a flange proximal to the sealed end. The flange can serve various purposes including, but not limited to, as a stopping reference point when joining the tube ends together, and aiding in opening the lumen (i.e., interior of the tube) after joining the tube ends together, etc.

Still in other embodiments, the thermoplastic tube further comprises a sealed vessel. Generally the sealed vessel is connected distal to the sealed end of the thermoplastic tube. However, it should be appreciated that the sealed vessel can be attached along any portion of the thermoplastic tube depending on a particular application and/or desired configuration. Within these embodiments, in some instances, the sealed vessel is a plastic bag.

Another aspect of the invention provides a thermoplastic cap that is adapted to provide a sealed thermoplastic tube end when a thermoplastic tube is connected to and hermetically sealed with the thermoplastic cap. The thermoplastic cap comprises:
  an orifice for receiving a thermoplastic tube, where the diameter of the orifice is adapted to be hermetically sealed with the thermoplastic tube when the thermoplastic tube is connected to the thermoplastic cap;
  a channel in fluid communication with the orifice and having a diameter that is different than the diameter of the orifice;
  a wall positioned between the orifice and the channel such that it is adapted for providing a stopping point during a process for joining or connecting the thermoplastic tube with the thermoplastic cap; and
  a sealed end at the end of the channel.

In some embodiments, the thermoplastic cap further comprises a flange on the outer surface. In this manner, one can use the flange to aid in opening the lumen after joining or connecting the thermoplastic tube ends.

Another aspect of the invention provides a method for connecting first and second thermoplastic tubes together transversely of the axis of each tube. The method generally comprises:
  forming molten thermoplastic ends from first and second thermoplastic tubes, where each of the first and the second thermoplastic tubes comprises:
    an inner diameter defining a lumen,
    an outer diameter; and
    a sealed end,
    where the cross section defined by the outer diameter is greater proximal to the sealed end relative to the cross section distal to the sealed end, and wherein the wall thickness defined by the difference between the outer and the inner diameter is greater proximal to the sealed end relative to the wall thickness distal to the sealed end; and
  moving the respective molten ends of the thermoplastic tubes together to form a joint between the first and the second thermoplastic tubes.

In some embodiments, each of the first and the second thermoplastic tube comprises a plurality of thermoplastic tubes. In this manner, a plurality of thermoplastic tubes are connected simultaneously.

Still in some other embodiments, the step of forming molten thermoplastic ends comprises contacting each of the sealed ends to a heat transferring material that is heated to a temperature that is at least equal to the melt temperature of the thermoplastic ends. It should be appreciated that other means of heating the thermoplastic tube that do not require a direct physical contact can also be used, such as heating with a laser beam, heating with air convection or flow, using radiated heat, using microwave heating, radio frequency heating, etc.

Still in other embodiments, methods of the invention further comprise substantially flattening the sealed end of each thermoplastic tube such that the lumen at a position to be connected, e.g., proximal to the sealed end, is substantially closed prior to the step of forming molten thermoplastic ends. When the sealed end of the thermoplastic tube is flattened and the internal volume approaches zero, the tip of the sealed end protrudes axially to extend the overall length of the tube towards the heating element. This protrusion is desirable, in that, if the opposite were to occur the likelihood of sterile connection is believed to be significantly lower. For example, if the closed tip were to invert, the melt flow extrusion would not occur entirely in a radial direction, as desired, but some component of the melt flow may move towards center of tubing, preventing sterility and self-opening. This collapsing feature also provides a minimum trapped volume between the tubing clamp and the heated end of the tube. If trapped volume exists during melt, the air or liquid may expand and/or vaporize thereby increasing the possibility of creating an external leak path not contained by the melt.

In some instances within these embodiments, the sealed end of the tube is designed to provide the above described protrusion during collapse. Any suitable tubing design that can accomplish this desired configuration can be employed in the invention. One exemplary method includes a tubing configuration where the most proximal end of the sealed tubing having the smallest wall thickness. Such a configuration causes the sealed end to initiate movement first as the tubing is collapsed. Furthermore, a small central protruding feature within the smallest wall thickness initiates collapse in the correct direction and prevents or reduces the likelihood of inversion collapse.

Within these embodiments, in some instances, the method further comprises opening the lumen after forming the joint between the first and the second thermoplastic tubes. Such opening of the lumen may occur without the aid of any external force, or it can be aided with an external force. Typically, opening of the lumen is carried out immediately after forming the joint between the first and the second thermoplastic tubes. However, it should be appreciated, that the lumen can be opened anytime after the joint between the first and the second thermoplastic tubes has been formed.

Yet in other embodiments, the step of contacting the thermoplastic tubes to the heat transferring material comprises providing a means for having molten thermoplastic flow substantially away from the lumen of each tube. This molten thermoplastic flow away from the lumen maintains aseptic conditions of the thermoplastic tube ends that are being connected.

Another aspect of the present invention provides a method for forming a sterile connection between a first thermoplastic tube and a second thermoplastic tube each comprising a sealed end. This method comprises:
  forming a molten thermoplastic end from each sealed end of the first and the second thermoplastic tubes such that each of the surface area of the molten thermoplastic to be joined is a substantially greater than the cross-sectional area of the sealed end; and
  moving the respective molten ends of the thermoplastic tubes together to form a joint between the first and the second thermoplastic tubes such that the joint comprises a flange formed from bonding of the molten thermoplastic from the first and the second thermoplastic tubes.

Without being bound by any theory, it is believed that having the surface area of the molten thermoplastic greater than that of the cross-sectional area of the sealed end of the thermoplastic tube allows facile and/or stronger adhesion between the first and the second thermoplastic tubes. The flange formed by the molten plastic can further serve as visual indication of a successful weld, thus providing means for quality control.

In some embodiments, the surface area of the molten thermoplastic flange is at least equal to the cross-sectional area of the sealed end. The surface area of the molten thermoplastic flange refers to the cross-sectional area, which is transversal to the tube axis, of the flange formed by the molten thermoplastic. Typically, however, the surface area of the molten thermoplastic flange extends beyond the outer diameter of the sealed end. In this manner, when the tubes are connected, the molten thermoplastic flange extends above the outer diameter of the joined thermoplastic tubes. Within these embodiments, the surface area of the molten thermoplastic is in one embodiment at least 250%, and in another embodiment at least 500%, greater than the cross-sectional area of the sealed end.

Still in some other embodiments, methods of the invention further comprise substantially flattening the sealed end of each thermoplastic tube such that the lumen at a position to be connected is substantially closed prior to the step of forming molten thermoplastic ends.

Yet in other embodiments, the step of forming molten thermoplastic ends comprises contacting each sealed end of the first and the second thermoplastic tubes to a hot plate thereby melting the sealed end to form the molten thermoplastic end. Within these embodiments, in some instances the step of contacting the thermoplastic tubes to the heat transferring material further comprises providing means for having molten thermoplastic flow substantially away from the lumen of each tube. In many instances, excess molten thermoplastic is formed by further advancing the thermoplastic tubing ends into the hot plate after initial contact has been made between the thermoplastic tube end and the hot plate. This produces excess molten thermoplastic flow away from the lumen and provides a sterile molten thermoplastic zone near the lumen for forming a sterile connection.

Yet another aspect of the invention provides a method for connecting first and second thermoplastic tubes together transversely of the axis of each tube, e.g., end-to-end connection, without a need for an external force to open an interconnecting lumen. Such method comprises:
  forming molten thermoplastic ends from first and second thermoplastic tubes, where each of the first and the second thermoplastic tubes comprises:
    an inner diameter defining a lumen,
    an outer diameter; and
    a sealed end, and
  moving the respective molten ends of the thermoplastic tubes together to form a joint between the first and the second thermoplastic tubes; and
  allowing the interconnecting lumen to open.

In some embodiments within this aspect of the invention, the thermoplastic wall thickness proximal to the sealed end has a sufficient elasticity modulus to cause an interconnecting lumen to open after the tubes have been connected. Typically, the wall thickness of the thermoplastic tube is such that the wall's elasticity modulus and/or the wall's elasticity modulus in combination with the elasticity modulus of the flange integral to the thermoplastic cap cause the interconnecting lumen to open without the need for any external force.

In some embodiments, the wall thickness proximal to the sealed end is at least about 1.2 mm. In other embodiments, the wall thickness is at least about 1.8 mm. Still in other embodiments, the wall thickness at least about 3.6 mm.

Still another aspect of the invention provides a thin thermoplastic melting plate adapted to be used with a heat weld thermoplastic tube connecting apparatus. The thermoplastic melting plate comprises a heat transferring material that is adapted for melting a thermoplastic tube to produce molten thermoplastic. The thermoplastic melting plate further comprises:
  a front surface;
  a back surface;
  an insulating material (i.e., heat insulating material) substantially covering the front and back surfaces;
  an exposed heat transferring material portion within the front and the back surfaces of the insulating material such that the exposed portion is adapted for melting the thermoplastic tube to produce molten thermoplastic; and
  an interface portion for operatively connecting the thermoplastic melting plate to the heat weld thermoplastic tube connecting apparatus.

In some embodiments, the insulating material comprises aluminum silicate, a heat insulating ceramic, or a combination thereof.

In other embodiments, the exposed heat transferring material portion is adapted for contacting the thermoplastic tube to produce molten thermoplastic.

Yet in other embodiments, the exposed heat transferring material portion is adapted to produce molten thermoplastic from the thermoplastic tube without directly contacting the thermoplastic tube.

Still in other embodiments, the interface portion is adapted to be operatively connected to a heating element of the heat weld thermoplastic tube connecting apparatus. In this manner, the heating element of the heat weld thermoplastic tube connecting apparatus heats the thermoplastic melting plate, thereby allowing the thermoplastic melting plate to heat and melt thermoplastics during its operation.

Yet another aspect of the invention provides a thermoplastic tube connecting apparatus comprising a removably attached thin heat transferring material that is adapted for melting a thermoplastic tube to generate a molten thermoplastic tube end. The thin heat transferring material comprises:
  a front surface;
  a back surface;
  an insulating material substantially covering the front and back surfaces;
  an exposed heat transferring material portion within the front and the back surfaces that is adapted for melting the thermoplastic tube to produce a molten thermoplastic tube end; and
  an interface portion for operatively connecting the thermoplastic melting plate to a heat weld thermoplastic tube connecting apparatus.

In some embodiments within this aspect of the invention, the exposed heat transferring material portion is adapted for contacting the thermoplastic tube to produce molten thermoplastic. In other embodiments, the exposed heat transferring material portion is adapted to produce molten thermoplastic from the thermoplastic tube without any direct contact with the thermoplastic tube.

Still in other embodiments, the interface portion is adapted to be operatively connected to a heating element of the heat weld thermoplastic tube connecting apparatus.

Still another aspect of the invention provides a thermoplastic tube connecting apparatus comprising:

a thermoplastic melting plate that is adapted for melting a thermoplastic tube thereby producing a molten thermoplastic tube end; and a thin film that is adapted for being placed between the thermoplastic tube and the thermoplastic melting plate such that the thermoplastic tube does not directly contact the thermoplastic melting plate during its operation.

In some embodiments, the thermoplastic melting plate is a thin heat transferring material.

The thin film can comprise polytetrafluoroethylene (Teflon®), thin malleable metallic sheets (such as aluminum foil and copper foil), polyester, Q Foil (available from EGC Enterprises Inc., Chardon, Ohio), or a combination thereof.

Still in other embodiments, the thermoplastic tube connecting apparatus further comprises a means for allowing a different portion of the thin film surface to come in contact with thermoplastic tubes during each thermoplastic tube connecting operation.

In some embodiments, the thermoplastic tube connecting apparatus further comprises a thin film traversing element for traversing, e.g., moving, the thin film relative to the thermoplastic melting plate thereby allowing a clean or different portion of the thin film to be contacted with the thermoplastic tubes during each thermoplastic tube connection operation.

Still another aspect of the present invention provides a method for connecting first and second thermoplastic tubes together transversely of the axis of each tube. This method of the invention comprises:

contacting the first and the second thermoplastic tubes to a thin film that is operatively connected to a thermoplastic melting plate to generate molten first and second thermoplastic tube ends; and moving the respective molten ends of the thermoplastic tubes together to form a joint between the first and the second thermoplastic tubes.

In some embodiments, each of the first and the second thermoplastic tubes comprises a plurality of thermoplastic tubes, thereby allowing multiple thermoplastic tubes to be sterilely connected simultaneously.

In some embodiments within this aspect of the invention, the method further comprises moving or traversing the thin film relative to the thermoplastic melting plate during and/or after each operation thereby allowing clean or different area of the thin film to be contacted with the thermoplastic tubes during each thermoplastic tube connection operation.

In other embodiments, the methods and apparatus provide for the connection of a plurality of first and second thermoplastic tubes using a plurality of think melting plates for generating the molten thermoplastic ends. In still other embodiments, a single thermoplastic melting plate is used for connecting a plurality of first and second thermoplastic tubes.

DETAILED DESCRIPTION OF THE INVENTION

The present invention provides various thermoplastic tubes, thermoplastic melting plates, thermoplastic tube connecting apparatus, and methods for using the same. Devices and methods of the present invention are particularly useful, although not necessary, in aseptic thermoplastic tube connection.

Some of the problems associated with conventional thermoplastic tube connecting methods are that the thermoplastic tube connection joints sometimes leak thus requiring carefully inspection and sometimes requiring the resulting products associated with the connection be discarded. Some of the methods and devices of the invention eliminate or greatly reduce the failure rate (i.e., leakage) of thermoplastic tube connection. Accordingly, methods and devices of the invention provide huge benefit to various medical procedures. For example, it is believed that in blood-banking applications in France, all thermoplastic tube connections made with currently available technology must be inspected, e.g., by pressurizing with air and holding the connected joint under water to check for leaks. Such inspection is time consuming. In addition, a significant amount of connected joints fail and have to be redone or the resulting products must be discarded, thereby adding to the overall cost and time, and loss of valuable blood materials. By eliminating or significantly reducing the failure rate, methods and devices of the invention significantly reduce the time and cost of connecting tubes.

The present invention will now be described with regard to the accompanying drawings which assist in illustrating various features of the invention. In this regard, the present invention generally relates to various devices and methods for connecting thermoplastic tube ends.

Figure 1A:
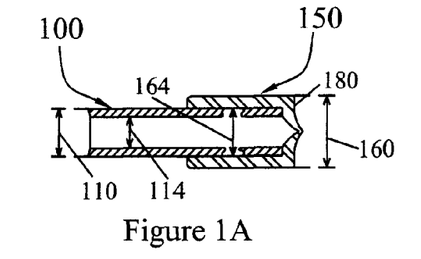
FIGS. 1A and 1B are a schematic, fragmentary longitudinal section view of a thermoplastic tube having a sealed end.
Figure 1B:
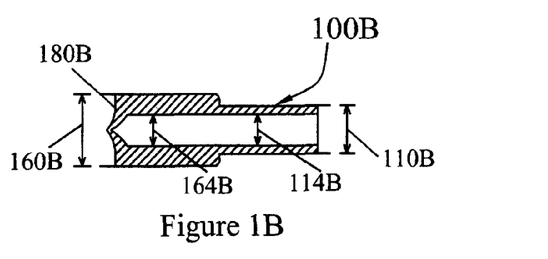

FIG. 1 is a schematic, fragmentary longitudinal section view of a thermoplastic tube having a sealed end. Two configurations are illustrated in FIGS. 1A and 1B. As can be seen in FIG. 1A, the distal end of the sealed end 180 comprises thermoplastic tube 100, which has an outer diameter 110 and an inner diameter 114. The thermoplastic tube 100 is inserted into and is hermetically sealed with a thermoplastic cap 150, which comprises the sealed end 180. The thermoplastic cap 150 has an outer diameter 160 and an inner diameter 164. The inner diameter 164 of thermoplastic cap 150 should be sufficiently large enough to accommodate thermoplastic tube 100 having the outer diameter 110. The inner diameter 164 of thermoplastic cap 150 should also be sufficiently small enough to form a hermetically sealed connection between thermoplastic tube 100 and thermoplastic cap 150.

In some embodiments, the inner diameter 164 of thermoplastic cap 150 is slightly smaller than the outer diameter 110 of thermoplastic tube 100 but is sufficiently large enough to allow insertion of thermoplastic tube 100 into thermoplastic cap 150, for example, by slightly expanding the inner diameter 164 with heat or by lubricating the outer surface of thermoplastic tube 100, for example, with a solvent thus forming a cohesive joint between thermoplastic components. Such configuration typically provides hermetically sealed connection between thermoplastic tube 100 and thermoplastic cap 150 without the need for any adhesive. Alternatively, when the inner diameter 164 is slightly larger than the outer diameter 110, an adhesive can be used to connect and/or hermetically seal thermoplastic tube 100 with thermoplastic cap 150. When an adhesive is used, such adhesive should be compatible with the desired application. Suitable adhesives include, but are not limited to, urethane adhesives, and solvent mediated adhesives.

FIG. 1B is a schematic illustration of one-piece longitudinal section view of a thermoplastic tube 100B having a sealed end 180B. In this embodiment, the inner diameter is relatively constant throughout, i.e., 114B and 164B are equal within the manufacturing limitation. However, the wall thickness defined by the difference between the outer diameter and the inner diameter is significantly different between the tube section distal to the sealed end and the tube section proximal to the sealed end. That is, the wall thickness defined by the difference between 160B and 164B is significantly higher than the wall thickness defined by the difference between 100B and 114B. Unless stated or the context requires otherwise, the term "proximal to the sealed end" refer to that portion of the thermoplastic tube having the wall thickness or the cross-sectional area that is substantially larger than the thermoplastic tube portion that is distal to the sealed end. Thus the terms "proximal" and "distal" are operational terms based on the wall thickness and/or the cross-sectional area of the tube. Unless stated or the context requires otherwise, the term "cross-sectional area" refers to the transversal cross-sectional area of the thermoplastic tube, i.e., cross-sectional area that is perpendicular to the longitudinal axis of the thermoplastic tube.

Referring again to FIGS. 1A and 1B, regardless of the configuration, in some embodiments, the outer diameter 160 that is proximal to the sealed end 180 is substantially greater than the outer diameter 110 that is distal to the sealed end 180. In addition, the wall thickness (defined by the difference between the outer diameter 160 and the inner diameter 164) proximal to the sealed end 180 is substantially greater than the wall thickness (defined by the difference in the outer diameter 110 and the inner diameter 114) distal to the sealed end 180.

Typically, thermoplastic tube 100 is flexible. However, it should be appreciated that the scope of the invention does not limit the thermoplastic tube 100 to be flexible. The material of thermoplastic tube 100, particularly the portion that is proximal to the sealed end 180, should be capable of becoming molten when heated. Conventional medical tubing materials, such as, but not limited to, thermoplastics, thermoplastic elastomers and PVC. Furthermore, the tubing can be co-extruded with a PVC core of higher melt temperature and an outer sleeve with similar melt temperature as compared to the cap component 150. The higher melt temperature core can allow a different melt flow characteristic to positively influence self-opening feature. In addition, the tubing can be co-extruded with a thermoplastic polyolefin core and thermoplastic outer sleeve allowing solvent bonding to the thermoplastic cap component 150. The polyolefin core can then allow a different melt flow characteristic to influence self opening. Moreover, the same property can be achieved using other thermoplastic resins co-extruded in a similar manner. Alternatively, the inverse can also be used where the co-extruded core can be a lower melt temperature thermoplastic ensuring a seal is formed in the center of the tubing that can be later opened if desired.

In some embodiments of the invention, thermoplastic cap 150 is used. Within such embodiments, in some instances both thermoplastic 100 and thermoplastic cap 150 have the same melting temperature. In other instances, thermoplastic cap 150 has a different melting temperature than thermoplastic tube 100. Within these instances, in some cases thermoplastic cap 150 has a higher melting temperature than thermoplastic tube 100. Still in other cases, thermoplastic cap 150 has a lower melting temperature than thermoplastic tube 100.

FIG. 2 illustrates a schematic, longitudinal section view of various thermoplastic cap configurations. Regardless of any particular configuration, thermoplastic cap 200 comprises an orifice 204 which is adapted for receiving a thermoplastic tube (not shown in FIG. 2) and a sealed end 280. The inner diameter of orifice 204 is adapted to receive and be hermetically sealed with the thermoplastic tube, when the thermoplastic tube is coupled with or connected to thermoplastic cap 200. In addition, thermoplastic cap 200 comprises channel 208 that is in fluid communication with orifice 204. Channel 208 may have the same inner diameter or a different inner diameter than the inner diameter of orifice 204. Thermoplastic cap 200 can also includes a wall 212 positioned between orifice 204 and channel 208. Wall 212 is adapted for providing a stopping point when a thermoplastic tube is inserted through orifice 204. However, it should be appreciated that a thermoplastic tube need not be inserted all the way to wall 212. All that is required is a sufficiently tight hermetic seal be formed between a thermoplastic tube and thermoplastic cap 200. As illustrated in FIG. 2, sealed end 280 can be of various shapes and configurations.

Figure 2A:
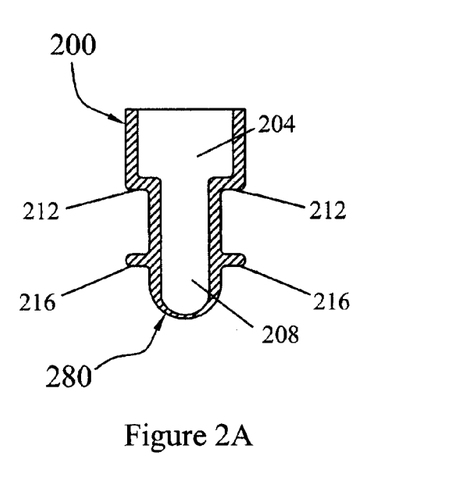
FIGS. 2A-2D are a schematic, longitudinal section view of various thermoplastic cap configurations.
Figure 2B:
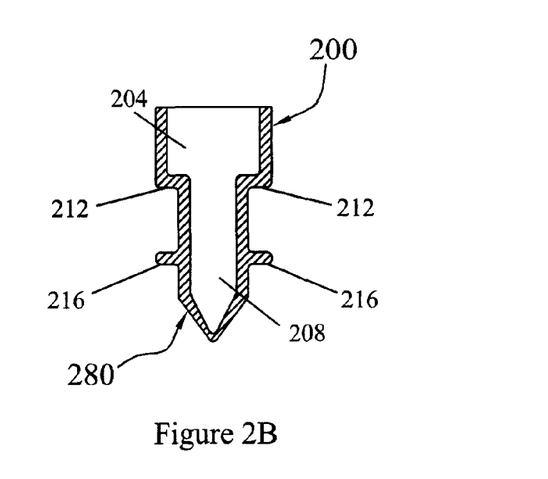
Figure 2C:
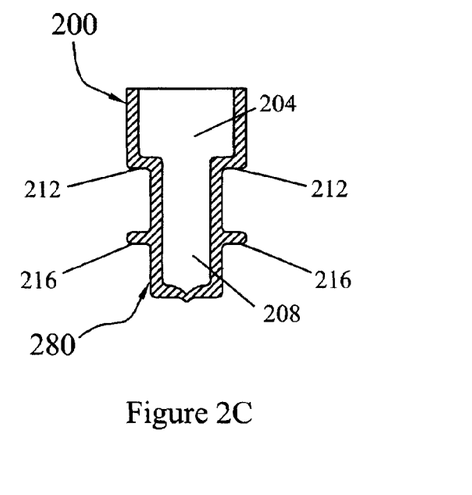
Figure 2D:
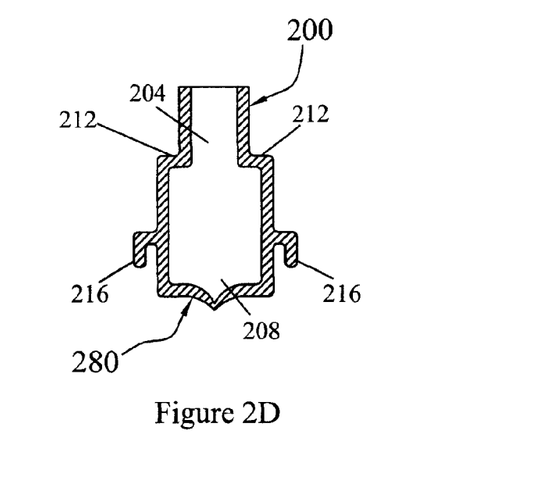

While the inner diameter of orifice 204 is typically larger than the inner diameter of channel 208, as illustrated in FIGS. 2A-C, in some embodiments, the inner diameter of orifice 204 is smaller than the inner diameter of channel 208. In this configuration, rather than inserting the thermoplastic tube to orifice 204, thermoplastic cap 200 is inserted into a thermoplastic tube. That is, the outer diameter of orifice 204 in FIG. 2D is such that it can be inserted into the thermoplastic tube and form a hermetic seal. Accordingly, the scope of the invention encompasses thermoplastic caps that receive a thermoplastic tube as well as thermoplastic caps that are inserted into a thermoplastic tube.

Optionally, thermoplastic cap 200 can also include a flange 216. Flange 216 can encompass the entire circumference of thermoplastic cap 200 or it can encompass only a portion of the circumference of thermoplastic cap 200. Flange 216 is useful for various purposes. For example, it can be used as a stopping point during melting of the sealed end 280 to form molten thermoplastic. That is, flange 216 can be used to allow formation of molten thermoplastic up to where flange 216 is located. Since the cross-section area of the thermoplastic is greater where flange 216 is located, joining of molten thermoplastic at flange 216 allows stronger joint connection as well as ease of joint formation due to its greater surface area for forming a joint connection. Furthermore, flange 216 can be used to aid in opening of the lumen after the thermoplastic tubes are connected. For example, one can use flange 216 to pull apart the lumen of connected thermoplastic tubes or the elasticity modulus associated with this flange could restore the lumen to the open condition following the joining of the tube ends.

Another aspect of the invention provides a method and devices for joining thermoplastic tubes in a sterile condition. In this aspect of the invention, thermoplastic tube configuration having a greater cross-sectional surface area proximal to the sealed end is provided. The present inventors have found that thermoplastics having a larger cross-sectional thermoplastic surface area allow stronger and/or easier connection between the thermoplastic tubes. Without being bound by any theory, it is believed that the ease, and/or reliability, of forming an airtight connection between thermoplastic tube ends is proportional to the cross-sectional thermoplastic surface area, i.e., thermoplastic tube ends having a larger cross-sectional thermoplastic surface area are easier to form reliable, strong and/or airtight connection. Accordingly, it is believed that the margin of error and/or the failure rate is inversely proportional to the cross-sectional thermoplastic surface area. Hence, some aspects of the invention reduce the margin of error for connecting thermoplastic tube ends by providing thermoplastic tube ends having a larger cross-sectional thermoplastic surface area relative to the conventional thermoplastic tubes that are typically used in forming a sterile connection. For example, conventional thermoplastic tubes that are used in medical procedures have inner diameter of about 0.16 inches with the cross-sectional thermoplastic area of about 6.2 mm$^2$ (0.6 mm wall thickness). By increasing the cross-sectional thermoplastic area to about 16 mm$^2$ (1.2 mm wall thickness) or to about 27 mm$^2$ (1.8 mm wall thickness), or to about 75 mm$^2$ (3.6 mm wall thickness), it has been found that a significantly stronger connection between thermoplastic tube ends can be formed. In addition, increasing the cross-sectional thermoplastic thickness also significantly reduces the rate of joint failure.

In one embodiment, a thermoplastic cap, such as those shown in FIG. 2 optionally having flange 216, is provided. As discussed above, the thermoplastic caps can be used to cap a conventional thermoplastic tube to provide a sealed end having a larger cross-sectional thermoplastic surface area. Alternatively, a thermoplastic cap such as those illustrated in FIG. 3 can be used to provide a larger cross-sectional thermoplastic surface area. It should be appreciated that thermoplastic caps in the accompanying Figures are for illustrative purposes only, and the scope of the invention includes any thermoplastic cap configuration that provides increased cross-sectional thermoplastic surface area and/or increased cross-sectional thermoplastic thickness.

One exemplary method for connecting a first and a second thermoplastic tubes together transversely of the axis of each tube is schematically illustrated in FIG. 3. In FIG. 3, the first thermoplastic tube 300 and the second thermoplastic tube 350 having thermoplastic caps 304 and 354 are shown. In this illustration, thermoplastic tubes 300 and 350 are inserted into and hermetically sealed with thermoplastic caps 304 and 354 to provide sealed ends 308 and 358, respectively. In this particular illustration, the thickness of thermoplastic caps 304 and 354 is substantially greater than the thickness of thermoplastic tubes 300 and 350. The cross-sectional thermoplastic surface area proximal to the sealed ends 308 and 358 is substantially greater than the cross-sectional surface area distal to the sealed end. In addition, the thermoplastic wall thickness is substantially greater proximal to the sealed end relative to the wall thickness distal to the sealed end.

Figure 3A:
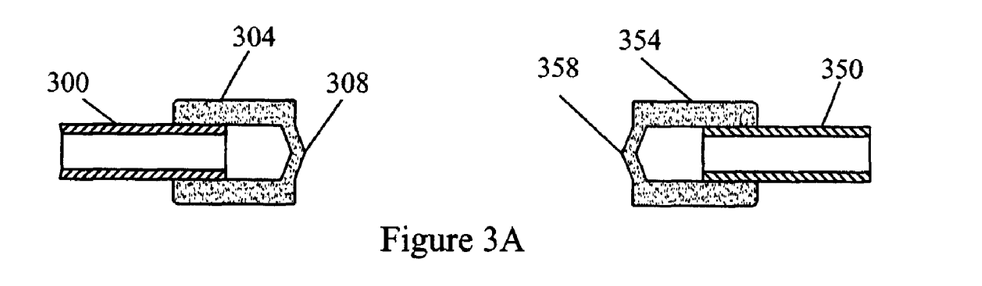
FIGS. 3A-3G are schematic illustrations of various steps in connecting a first and a second thermoplastic tubes together transversely of the axis of each tube.
Figure 3B:
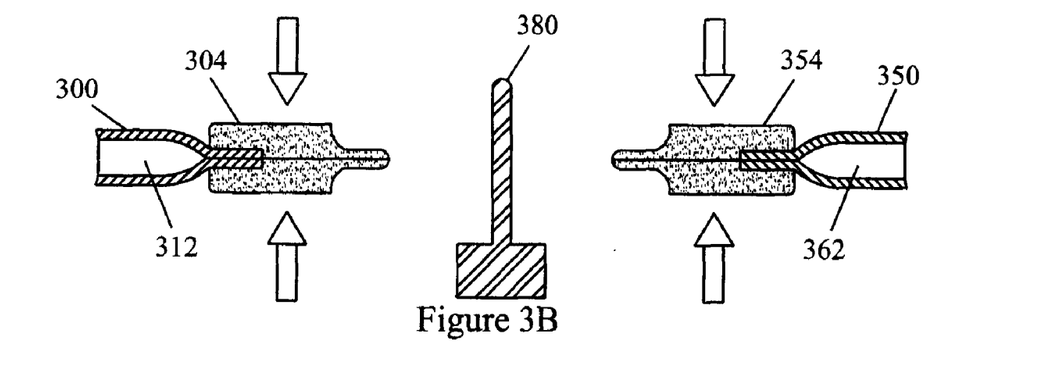

For connecting first thermoplastic tube 300 with second thermoplastic tube 350, the sealed ends 308 and 358 are optionally, and preferably, compressed as shown in FIG. 3B. This compression closes the lumens (or tube interiors) 312 and 362 proximal to the sealed ends 308 and 358, respectively. Such closure prevents the lumen of tubes 300 and 350 from filling with molten thermoplastic while being pressed into the hot plate as described below. In addition, such closure also prevents the lumens from being exposed to the atmosphere and maintains the thermoplastic tubes in an aseptic condition. Additionally, such closure allows removal of interior contents from the molten thermoplastic preventing external leaks due to expanding tubing contents with rising temperature.

Figure 3C:
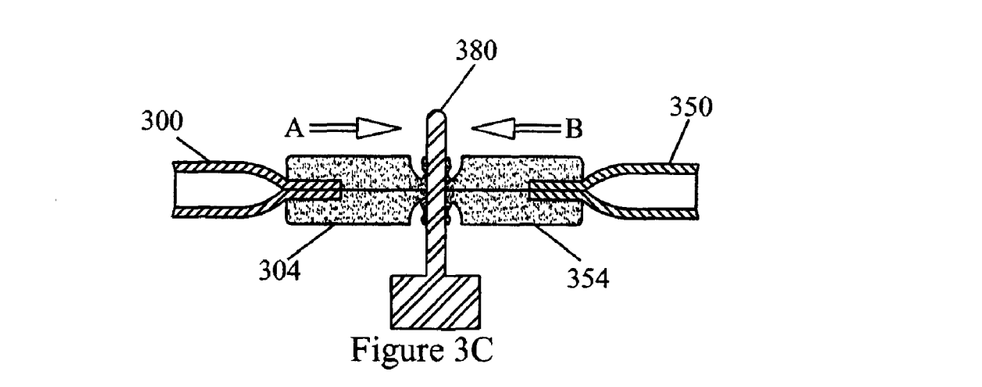

The sealed ends 308 and 358 are then heated, either by a direct contact with a heated plate 380 or by other heating means known to one skilled in the art (not shown), including non-direct contact means such as those discussed above. As shown in FIG. 3C, thermoplastic tubes are pressed into hot plate 380 in a direction shown by arrows A and B. This pressing of the thermoplastic tubes into hot plate 380 melts the thermoplastic at the sealed end to produce molten thermoplastic. It should be appreciated that the sealed ends 308 and 358 can optionally be cut using a cutting blade, which may be the same as hot plate 380, prior to producing molten thermoplastic. Preferably the cutting blade is heated to allow simultaneous cutting and melting of the thermoplastic. As used herein, the term "molten thermoplastic" refers to both melted thermoplastic as well as softened thermoplastic resin that is capable of adhering to other molten thermoplastic.

Figure 3D:
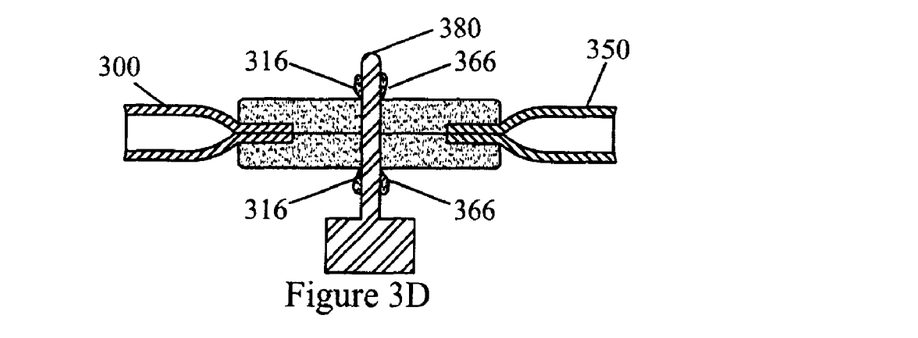
Figure 3E:
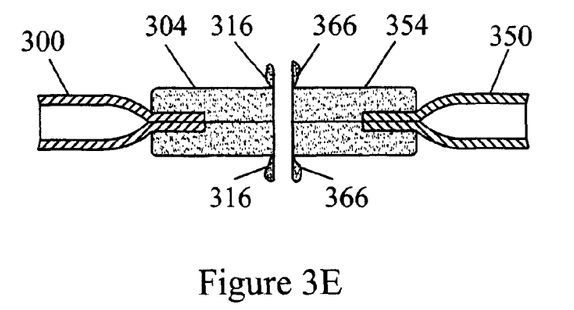
Figure 3F:
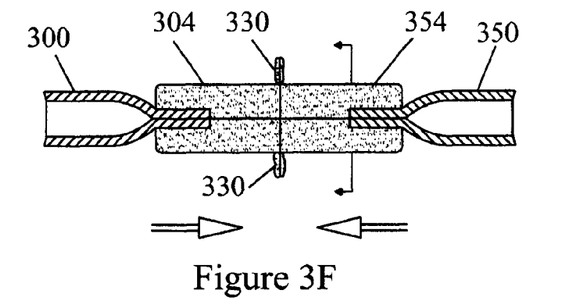

FIG. 3C shows molten thermoplastic 316 and 366 flowing away from the compressed lumens of thermoplastic tubes and caps. It should be appreciated that the likely contaminated surface portions 308 and 358 of caps 304 and 354 are the first portions of the cap to become molten. As the surface regions melt and flow away from the lumen, any contaminants contained thereon are effectively flushed or removed away from the lumen thus maintaining lumen sterility. In some embodiments of the invention, it is advantageous to produce excess molten thermoplastic 316 and 366 as shown in FIG. 3D. Excess molten thermoplastic flow further helps carry away from the lumen any contaminants that might have been on the surface of the tube or the cap. After producing molten thermoplastic, hot plate 380 is removed as shown in FIG. 3E, while maintaining airtight closure of interior of thermoplastic tubes 300 and 350. The molten ends are then contacted with one another as shown in FIG. 3F to form a joint between thermoplastic tubes 300 and 350. The thermoplastic tubes may optionally be further advanced in the direction of arrows A and B (see FIG. 3C), thus producing additional molten thermoplastic flow and purging the molten surfaces of any air born contaminant that may have landed on the molten surface following removal of hot plate 380. When excess molten thermoplastic 316 and 366 is present, the resulting joint between thermoplastic tubes 300 and 350 may include flange 330. When excess molten thermoplastic is present, it provides a greater surface area for forming a connecting joint. As discussed above, the greater surface area reduces the rate of joint failure as well as providing a stronger and/or easier joint formation.

Figure 3G:
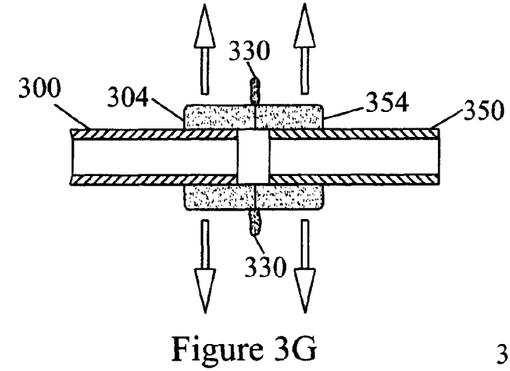

After joining the molten thermoplastic ends together, the external force (e.g., clamp) is removed allowing the lumen to regain its original shape. See, for example, FIG. 3G. In some embodiments, the thermoplastic wall proximal to the sealed end has a sufficient elasticity modulus to open the interconnecting lumen without a need for any external force. Generally the required elasticity modulus is a result of the thermoplastic tube's wall thickness and relatively low melting temperature as compared to the sealed end. In other embodiments, flange 330 can be used to aid in opening the lumen, e.g., by pulling flange 330 away from the lumen or by virtue of the elasticity modulus of the flange and/or the thermoplastic tubes themselves. In other embodiments, elastic modulus of flange 216 maybe used to open the lumen without any external force.

Figure 3H:
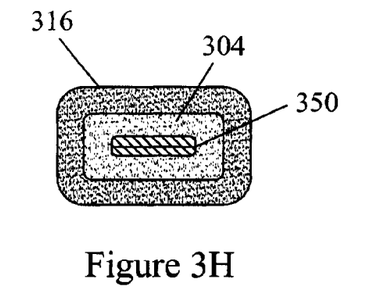
FIG. 3H is a transversal cross-sectional illustration of one of the thermoplastic tubes shown in FIG. 3D.

FIG. 3H is a transversal cross-sectional view of thermoplastic tube 300 shown in FIG. 3D. During its contact with hot plate 380 (not shown in FIG. 3H, but see FIG. 3D), molten thermoplastic is produced proximal to the sealed end 308. As thermoplastic tube 300 is pressed into hot plate 380, molten thermoplastic flows away from the interior of thermoplastic tube 300. Such molten thermoplastic flow maintains aseptic condition of the interior of thermoplastic tube 300. Generally, when excess molten thermoplastic flow is used, the surface area of the molten thermoplastic is at least about 100% greater, preferably at least about 250% greater, and more preferably at least about 500% greater, than the cross-sectional area of the sealed end. In one particular example, when excess molten thermoplastic flow is used, the surface area of the molten thermoplastic is from about at least 200% to about 800% greater than the cross-sectional area of the sealed end.

Suitable thermoplastic tube connecting apparatuses are well known to one skilled in the art and include, but are not limited to, those discussed in the Background of the Invention section as well as U.S. Pat. Nos. 6,341,637; 6,026,882; 6,679,529; 6,913,056; 4,443,215; 4,412,835; 4,507,119; 5,345,070; and PCT Publication Nos. WO 82/02528; and WO 02/087491, all of which are incorporated herein by reference in their entirety.

In conventional thermoplastic tube connecting apparatuses that use a thermoplastic melting plate, the surface area of the thermoplastic melting plate that is heated during operation is significantly larger than the area needed to produce molten thermoplastic from the thermoplastic tube. This results in a significantly higher energy requirement than necessary since the excess heat dissipates from the heated surface area of the thermoplastic melting plate without being used.

Figures 4A, 4B, 4C:
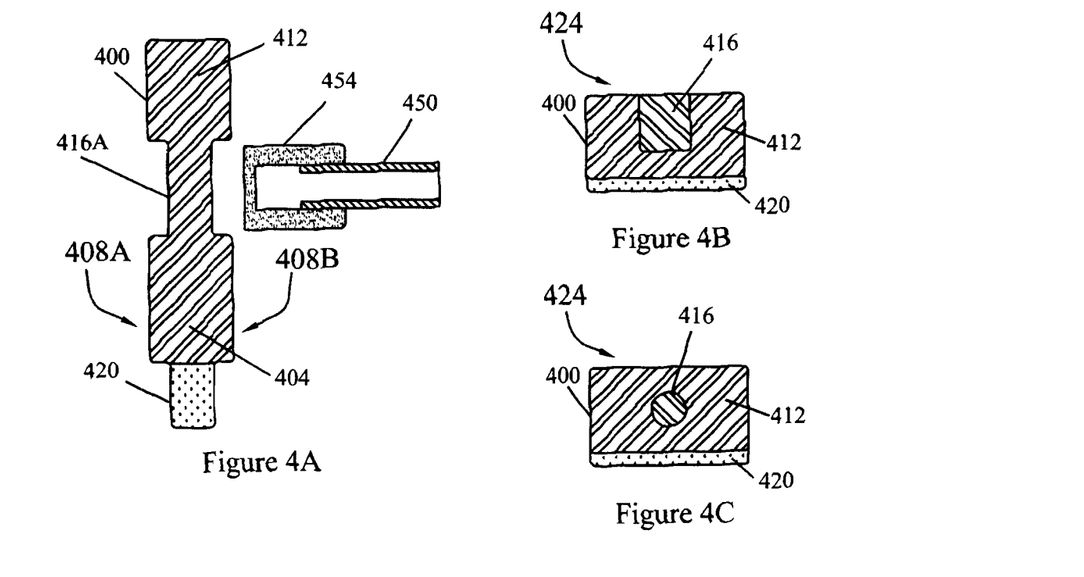
FIG. 4A is a schematic cross-sectional view of a thermoplastic melting plate and the thermoplastic tube.
FIGS. 4B and 4C are a side view of various thermoplastic melting plate configurations.

Accordingly, another aspect of the present invention provides a thermoplastic melting plate that is designed to significantly reduce or eliminate unnecessary heat consumption during its operation. In some embodiments, a thermoplastic melting plate that is adapted to be used with a heat weld thermoplastic tube connecting apparatus is provided. FIGS. 4A-4C illustrate some embodiments of the thermoplastic melting plate of the invention. As can be seen, the thermoplastic melting plate 400 comprises a heat transferring material 404 that is adapted for melting a thermoplastic tube to produce molten thermoplastic. As used herein, the term "heat transferring material" refers to any material of a component of an apparatus that is used to produce molten thermoplastic from the thermoplastic. In addition, thermoplastic melting plate 400 comprises a front surface 408A; a back surface 408B; an insulating material 412 substantially covering front surface 408A and back surface 408B; an exposed heat transferring material portion (416A and 416B in FIGS. 4A and 416 in FIGS. 4B and 4C) within the insulating material 412 such that the exposed heat transferring material portions are adapted for melting the thermoplastic tube 450 and the thermoplastic cap 454 to produce molten thermoplastic; and an interface portion 420 for operatively connecting thermoplastic melting plate 400 to a heat weld thermoplastic tube connecting apparatus (not shown). Typically, interface portion 420 is adapted to be operatively connected to a heating element of the heat weld thermoplastic tube connecting apparatus (not shown).

The thermoplastic melting plate can be made of any material that can conduct heat. Exemplary materials that are suitable for thermoplastic melting plates include metals, heat transferring ceramics, metal alloys, as well as other materials that are known heat conductors, such as a flash heater available from Watlow Electric Manufacturing Company (St. Louis, Mo.). In one specific embodiment, the thermoplastic melting plate is adapted for use with tube connecting apparatuses such as the Terumo Sterile Tubing Welder, Model SC-201A (available from Terumo Medical Corp. Somerset, N.J., U.S.A.). In one embodiment, the thermoplastic melting plate is a thin plate that can optionally be used to both heat and cut thermoplastic tubes.

In other embodiments, the thermoplastic melting plate can be a thin plate that is sized to correspond to the area to be sealed. Such a plate does not need to have any insulating material and can heat and cool very rapidly due to its thinness.

In other embodiments, thermoplastic melting plates of the invention are adapted to be useful in any thermoplastic connecting apparatus that is schematically illustrate in FIG. 3 as well as those that do not require a direct contact to produce molten thermoplastic. As will be recognized, in embodiments where the thermoplastic tube is not directly contacted to the thermoplastic melting plate, the thermoplastic melting plate is heated to a temperature sufficient to melt the thermoplastic tube when it is placed near the thermoplastic melting plate.

The insulating material, when used, substantially covers the portion of the thermoplastic melting plate that is not used in thermoplastic tube connection operation. In one embodiment, the insulating material comprises aluminum silicate, a heat insulating ceramic, or a combination thereof.

In some embodiments, the thermoplastic melting plate can also be used to cut the thermoplastic tube. In such embodiments, the thermoplastic melting plate comprises an edge 424 (see FIG. 4B) that is sufficiently shaped when heated to cut a thermoplastic tube.

Another aspect of the invention provides a thermoplastic tube connecting apparatus comprising the thermoplastic melting plate disclosed herein.

One of the problems associated with a hot plate thermoplastic tube connection apparatus is the potential for degraded plastic and/or molten plastic to build up on the hot plate. In some cases, such problem is eliminated by using a disposable hot plate. However, this solution adds to the overall cost and time for connecting thermoplastic tubes by requiring the hot plate to be replaced after each operation.

Figure 5A:
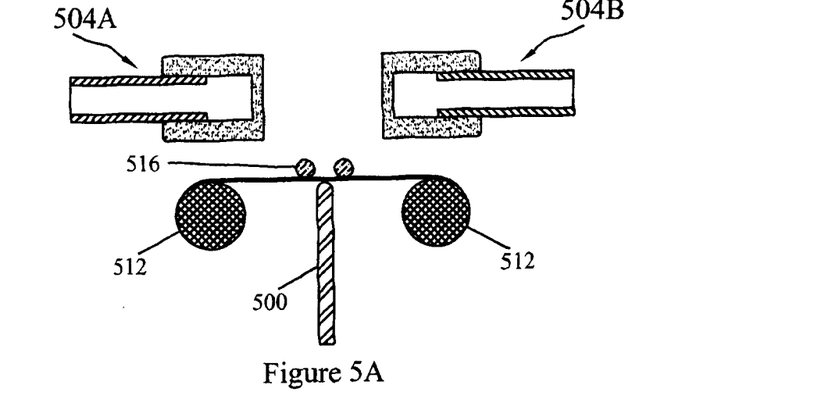
FIGS. 5A and 5B are cross-sectional view of a thermoplastic tube connecting apparatus comprising a thin film that is designed to prevent a direct contact between a hot plate and a thermoplastic tube.
Figure 5B:
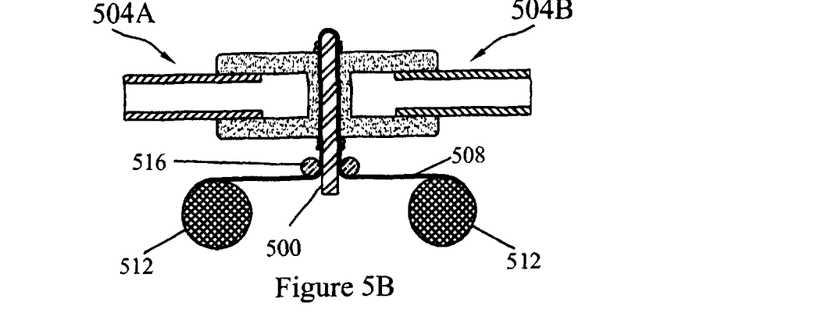

Accordingly, another aspect of the present invention provides a device and a method for eliminating degraded plastic and/or molten plastic from building up on the hot plate without a need for using a disposable hot plate. As illustrated in FIGS. 5A and 5B, one embodiment of such a thermoplastic tube connecting apparatus comprises a thermoplastic melting plate 500 that is adapted for melting a thermoplastic tube (504A and 504B) thereby producing a molten thermoplastic tube end; and a thin film 508 that is adapted for being placed between the thermoplastic tubes 504A and 504B, and the thermoplastic melting plate 500 such that the thermoplastic tubes do not come in direct contact with thermoplastic melting plate 500 during its operation.

Thin film 508 can be comprised of any material that readily conducts heat and is sufficiently strong enough to withstand tear during operation. When thin film 508 is used, thermoplastic melting plate 500 should not have any sharp edges as any sharp edge may tear thin film 508. Accordingly, in some embodiments, thermoplastic melting plate 500 has a rounded dull edge which reduces the risk of causing any tear of thin film 508. Exemplary materials that are suitable for thin film 500 include, but are not limited to, thin malleable metallic sheets (such as aluminum foil and copper foil), polytetrafluoroethylene, polyester, Q Foil (available from EGC Enterprises Inc., Chardon, Ohio), and a combination thereof.

The thermoplastic tube connecting apparatus can also include a roller, a drum, a cartridge, or other mechanical means known to one skilled in the art that allows a different portion of thin film 508 to come in contact with thermoplastic tubes during subsequent thermoplastic tube connecting operations. Such mechanism is schematically represented as item 512 in FIGS. 5A and 5B. The amount of thin film 508 advancement during each thermoplastic tube connection operation can be controlled by a computer (not shown) or it can be controlled by a mechanical means such as a sprocket or a gear mechanism that is spaced according to the amount of thin film 508 advancement desired. Alternatively, friction based rollers can be used to advance the desired amount of thin film 508. Another method is to provide a plurality of sprocket drive holes (not shown) near the edge of thin film 508. Such sprocket drive holes can be precision punched to maintain a uniform spacing and to allow proper advancement of thin film 508 with each thermoplastic tube connection operation using, for example, tractor drive mechanism (not shown).

Regardless of the mechanism used, each thermoplastic tube connection operation allows a fresh new surface area of thin film 508 to come in contact with thermoplastic tubes, thereby preventing any direct contact between thermoplastic melting plate 500 and thermoplastic tubes 504A and 504B. Such operation prevents any build up of degraded plastic and/or molten plastic on hot plate 500 and provides a clean surface for thermoplastic melting without the need for using a disposable thermoplastic meting plate.

The thermoplastic tube connecting apparatus can also include one or more guides 516 that are adapted to allow thermoplastic hot plate 500 to be properly positioned and allow thin film 508 to be operatively connected to thermoplastic hot plate 500. Guide 516 can be a separate roller, drum, or other mechanical device known to one skilled in the art. Alternatively, guide 516 can be part of a thermoplastic tube holder as discussed in detail below.

Figures 5C, 8:
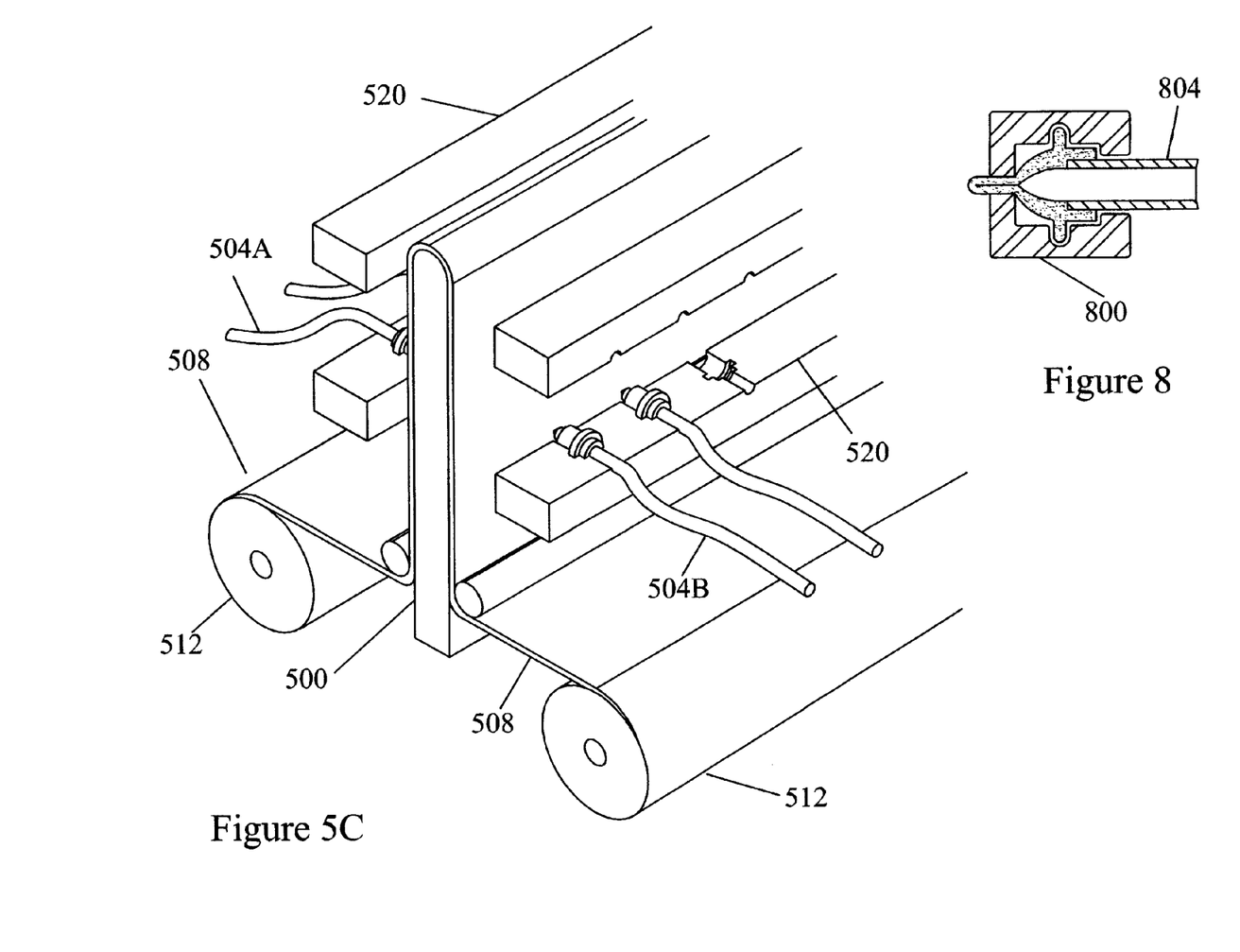
FIG. 5C is a perspective view of a thermoplastic tube connecting apparatus of FIGS. 5A and 5B comprising a plurality of thermoplastic tube holders that can be used to simultaneously connect a plurality of thermoplastic tubes.
FIG. 8 is a close-up cross-sectional view of a thermoplastic tube holder.

As shown in FIG. 5C, thermoplastic tube connecting apparatus of the invention can comprise a thermoplastic tube holder 520 that can hold a plurality of thermoplastic tubes (or a plurality of thermoplastic tube holders). This configuration allows simultaneous connection of a plurality of thermoplastic tubes. This is particularly useful with the thermoplastic tube connecting apparatus that comprises a thin film 508 which eliminates a need for disposable thermoplastic melting plate and/or the direct contact between thermoplastic melting plate 500 and thermoplastic tubes 504A and 504B. In FIG. 5C, thermoplastic tube holder 520 can also serve as a guide that allows thermoplastic hot plate 500 to be properly positioned.

Although FIG. 5C shows a single thermoplastic melting plate 500 with thin film 508, it is understood that multiple tube connections can be made with a plurality of thin thermoplastic melting plates, wherein each plate is associated with a pair of the multiple tube connections.

Figure 6:
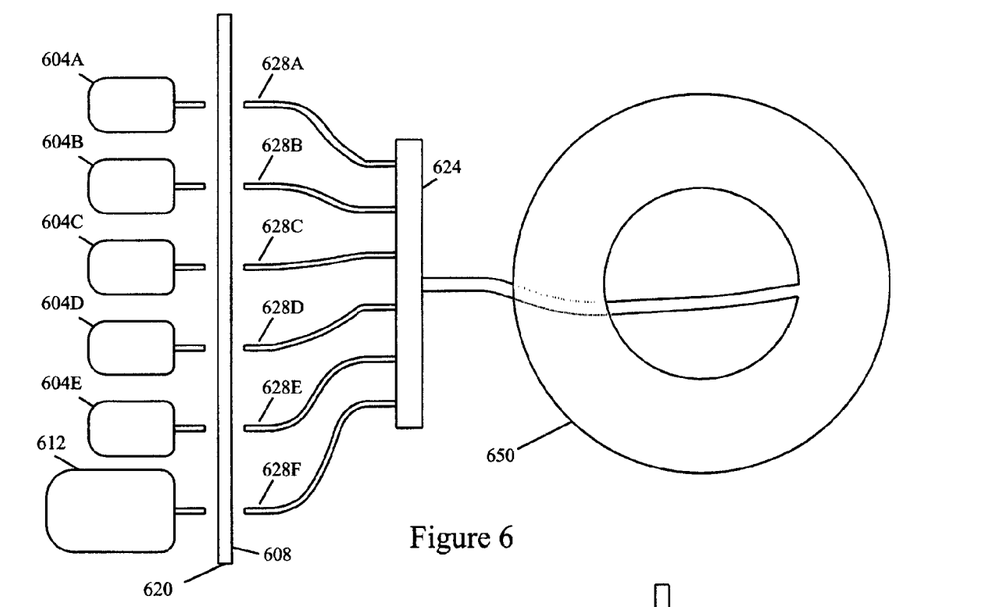
FIG. 6 is a schematic illustration of simultaneously connecting a plurality of thermoplastic tubes such as in platelet separation from buffy coats.
Figure 7:
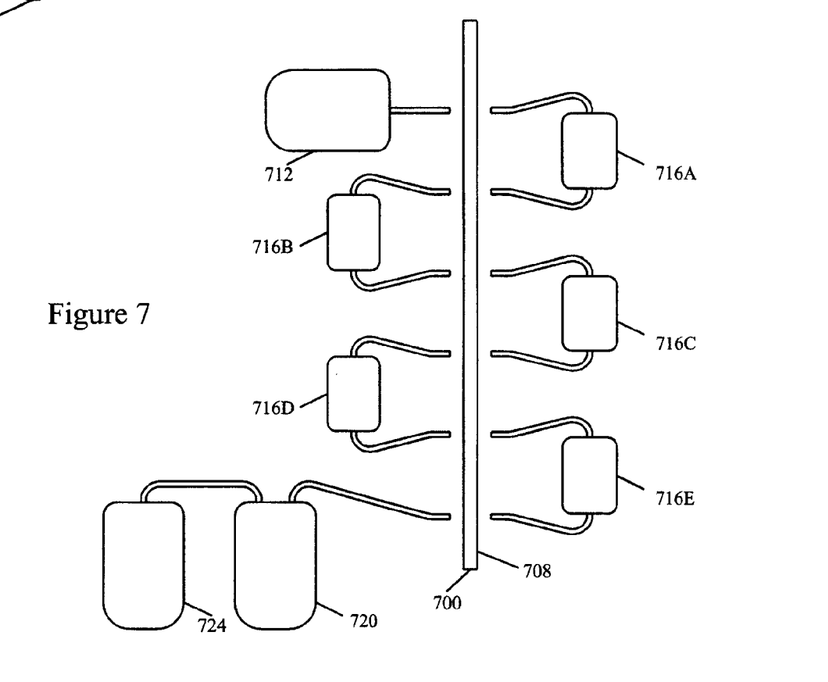
FIG. 7 is another schematic illustration of simultaneously connecting a plurality of thermoplastic tubes.

Achieving simultaneous multiple thermoplastic tube connection is advantageous in various medical procedures compared to the conventional sterile thermoplastic tube connection methods that use a single costly disposable blade for each connection. As shown in FIGS. 6 and 7, use of thin film 608 and 708, respectively, eliminates the need for replacing the hot plate 600 and 700, respectively, after each tube connection operation. In part, thin film 608 and 708 prevents molten tubing plastic from adhering to hot plate 600 and 700, respectively. FIGS. 6 and 7 illustrate simultaneous multiple tube connection that can be used in various medical procedures, for example, for removing platelets from buffy coats previously separated from whole blood. One example of currently available apparatus for removing platelets is the Orbisac System available from Gambro BCT, Inc. (Lakewood, Colo., USA). Buffy coat, produced from a whole blood donation, is a combination of platelets and white blood cells, as well as small amounts of red blood cells and plasma.

As a brief background, in the mid-1970's, European blood centers began to remove the buffy coat from separated red blood cells. It was discovered that the buffy coat contained a high concentration of platelets, a blood component vital to blood clotting.

The majority of platelets collected during a whole blood donation are found in the buffy coat layer, which settles between red blood cells and plasma during centrifugation. To extract as many of these platelet as possible, buffy coats are pooled from many donations and re-spun in a centrifuge to separate the platelets from the rest of the buffy coat. The platelets collected contain some white blood cells even after centrifugation, so the platelets are filtered to remove white blood cells before storage and transfusion. This process is called leukoreduction.

Platelets help the blood to clot. People with certain diseases like thrombocytopenia, leukemia, and other cancers have a reduced number of platelets in their bloodstreams. Without adequate platelets, they bleed abnormally and bruise easily. Regular platelet transfusions are essential treatment for these and other patients. Typically, the process to create pooled, leukoreduced platelets from whole blood is time-consuming, labor-intensive and requires many manual steps.

Processing whole blood buffy coat platelets requires multi-step, post-donation processes: pooling, centrifugation, expression, and filtration. These manual processes are labor-intensive and time consuming. As expected, anytime a task is performed manually, there is an increased risk of processing errors. Whole blood donations are separated into components via gravitational force in a centrifuge. The force of the centrifuge causes the whole blood to separate into layers based on cell density. The upper layer captured in the centrifuge is plasma. The middle layer is the buffy coat. The bottom, heaviest layer is packed red blood cells. There are various automated apparatuses to perform the buffy coat processing steps, such as the Orbisac System. Typically, these apparatuses perform various tasks, such as pooling, centrifugation, expression, and filtration.

Some embodiments of the thermoplastic tube connecting apparatus of the invention allow simultaneous multiple thermoplastic tube connection, such as those useful in collecting platelets and processing buffy coats pooled from many blood donations. As shown in FIG. 6, five (5) different bags (604A to 604E) each containing buffy coat are simultaneously connected to a centrifuge bag 650 used in combination with the Orbisac System, using hot plate 600 and a thin film 608 as described herein. In addition, a bag containing platelet storage solution or plasma 612 is also simultaneously connected to the centrifuge device 650. Thermoplastic tubes from bags 604A-604E and 612 are placed such that they are properly positioned for connection, see for example FIG. 5C. It should be appreciated that some devices may require the bags be connected in series such as that depicted in FIG. 7. A tube holder (520 in FIGS. 5C and 800 in FIG. 8), which optionally, and preferably, clamps and closes the lumen, holds the thermoplastic tubes (504 in FIGS. 5C and 804 in FIG. 8) in proper position. The tube holder (520 in FIGS. 5C and 800 in FIG. 8) also moves tubing ends against an optionally thin film 508 covered hot plate 500 to produce molten thermoplastic tube ends. After removing the hot plate 500, the tube holder 520 moves the molten thermoplastic tube ends together to form joint connections. A tubing manifold 624 connects the plurality of thermoplastic tubes 628A-628F to the centrifuge bag (or other container) 650.

After connecting buffy coat bags 604A-604E to tubing manifold 624, buffy coats, along with the storage solution, are pooled in the centrifuge bag 650 and the platelets are separated from the rest of the buffy coat. The collected platelets are then transferred to platelet storage bag 612 and then optionally filtered to further remove white blood cells.

Alternatively, as shown in FIG. 7, a platelet storage solution bag 712 and a plurality of buffy coat bags (e.g., 716A-716E) are connected as shown using the thermoplastic tube connecting apparatus of the invention. Formation of such plurality tubing connections are described herein. In FIG. 7, buffy coats are pooled in to a centrifuge bag 720. The contents of bag 720 is then centrifuged, e.g., in a conventional bucket centrifuge, to separate the platelets (centrifuge step not shown). The collected platelets are again optionally filtered to further remove white blood cells and are then transferred to a storage bag 724. Unlike the process illustrated in FIG. 6, process of FIG. 7 does not require a tubing manifold 624.

Additional objects, advantages, and novel features of this invention will become apparent to those skilled in the art upon examination of the following examples thereof, which are not intended to be limiting.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for connecting first and second thermoplastic tubes together transversely of the axis of each tube comprising:
   forming molten thermoplastic ends from first and second thermoplastic tubes, wherein each of the first and the second thermoplastic tubes comprises:
   an inner diameter defining a lumen,
   an outer diameter; and
   a sealed end cap, wherein said cap has an outer diameter substantially greater than said outer diameter of said tube, and wherein the wall thickness defined by said inner diameter of said tube and said outer diameter of said cap is substantially greater than a wall thickness of said tube,
   moving the respective molten ends of the sealed end caps together to form a joint between the first and the second thermoplastic tubes, and
   substantially flattening the sealed end caps of each thermoplastic tube such that the lumen at a position to be connected is substantially forming molten thermoplastic ends.

2. The method of claim 1, wherein said step of forming molten thermoplastic ends comprises contacting each of the sealed end caps to a heat transferring material that is heated to a temperature at least equal to the melt temperature of the end caps.

3. The method of claim 1, wherein said step of forming molten thermoplastic ends comprises heating each of the sealed end caps to temperature at least equal to the melt temperature of the thermoplastic ends.

4. The method of claim 1 further comprising opening the lumen after forming the joint between the first and the second thermoplastic tubes.

5. The method of claim 2, wherein said step of contacting the thermoplastic tubes to the heat transferring material further comprises providing means for having molten thermoplastic flow substantially away from the lumen of each tube.

6. A method for forming a sterile connection between a first thermoplastic tube and a second thermoplastic tube each comprising a sealed end cap, each cap having an outer dimension larger than an outer dimension of said cap's respective tube, said method comprising:
   forming a molten thermoplastic end from each sealed end cap of the first and the second thermoplastic tubes such that the surface area of the molten, thermoplastic is greater than the cross-sectional area of the sealed end;
   moving the respective molten ends of the thermoplastic tubes together to form a joint between the first and the second thermoplastic tubes such that the joint comprises a flange formed from bonding of the molten thermoplastic from the first and the second thermoplastic tubes, and
   substantially flattening the sealed end cap of each thermoplastic tube such that the lumen at a position to be connected is substantially closed prior to said step of forming molten thermoplastic ends.

7. The method of claim 6, wherein said step of forming molten thermoplastic ends comprises contacting each sealed end cap of the first and the second thermoplastic tubes to a hot plate thereby melting the sealed end to form the molten thermoplastic end.

8. The method of claim 7, wherein said step of contacting the thermoplastic tubes to the heat transferring material further comprises providing means for having molten thermoplastic flow substantially away from the lumen of each tube.

9. A method for forming a sterile connection between a first thermoplastic tube and a second thermoplastic tube each tube comprising a sealed end cap, each cap having an outer dimension larger than an outer dimension of said cap's respective tube, said method comprising:
   forming a molten thermoplastic end from each sealed end cap of the first and the second thermoplastic tubes;
   substantially flattening the sealed end caps of each thermoplastic tube such, that the lumen at a position to be connected is substantially closed prior to said step of forming molten thermoplastic ends; and
   moving the respective molten end caps of the thermoplastic tubes together to form a joint between the first and the second thermoplastic tubes such that the joint comprises a flange formed from bonding of the molten thermoplastic from the first and the second thermoplastic tubes, wherein said step of moving the respective molten ends together results in the cross sectional area of the sealed end caps being substantially greater than the cross sectional area of the walls of the tube proximal to the sealed end.

10. A method for connecting first and second thermoplastic tubes together transversely of an axis of each tube without a need for an external force to open an interconnecting lumen, said method comprising:
   forming first and second thermoplastic tubes, wherein each of the first and the second thermoplastic tubes comprises:
   an inner diameter defining a lumen,
   an outer diameter; and a sealed thermoplastic end cap, said cap having an outer dimension larger than said outer diameter of said thermoplastic tube, wherein the wall thickness defined by said inner diameter and said outer dimension proximal to said sealed end has a sufficient elasticity modulus to open an interconnecting lumen after the tubes have been connected;

substantially flattening the sealed end caps of each thermoplastic tube such that the lumen at a position to be connected is substantially closed;

melting said thermoplastic end caps;

moving the respective molten end caps of the thermoplastic tubes together to form a joint between the first and the second thermoplastic tubes; and allowing the interconnecting lumen to open.

11. The method of claim 10, wherein the wall thickness of the cross-sectional area proximal to the sealed end is at least about 0.7 mm.

* * * * *